US010661058B2

(12) United States Patent
Woehr

(10) Patent No.: US 10,661,058 B2
(45) Date of Patent: *May 26, 2020

(54) NEEDLE SAFETY DEVICE AND ASSEMBLY

(71) Applicant: B. Braun Melsungen AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,636

(22) Filed: Apr. 10, 2017

(65) Prior Publication Data

US 2017/0209675 A1 Jul. 27, 2017

Related U.S. Application Data

(63) Continuation of application No. 13/195,492, filed on Aug. 1, 2011, now Pat. No. 9,782,546.

(Continued)

(51) Int. Cl.
*A61M 25/06* (2006.01)
*A61M 5/32* (2006.01)

(52) U.S. Cl.
CPC ...... *A61M 25/0618* (2013.01); *A61M 5/3273* (2013.01); *A61M 25/0606* (2013.01); *Y10T 29/49826* (2015.01)

(58) Field of Classification Search
CPC ............ A61M 5/3273; A61M 25/0606; A61M 25/0612; A61M 25/0618; A61M 25/0625;

(Continued)

(56) References Cited

U.S. PATENT DOCUMENTS 4,929,241 A 5/1990 Kulli
5,135,504 A 8/1992 McLees
(Continued)

FOREIGN PATENT DOCUMENTS

AU 2009227517 10/2010
AU 2011287917 3/2013
(Continued)

OTHER PUBLICATIONS

Examination Report on corresponding foreign application (EP Application No. 11736297.0) from the European Patent Office dated Dec. 22, 2017.

(Continued)

*Primary Examiner* — William R Carpenter
*Assistant Examiner* — Larry R. Wilson
(74) *Attorney, Agent, or Firm* — Klein, O'Neill & Singh, LLP

(57) ABSTRACT

Safety intravenous catheters (IVCs) are disclosed herein having a catheter hub with a catheter tube, a needle with a needle hub, and a needle guard. The needle guard is configured to be positioned at least partially within an interior space of the catheter hub and is retained thereto by mechanical engagement between the two. Following removal of the needle from the catheter hub, the needle guard is configured to disengage from the catheter hub and attach over a tip of the needle to shield the needle tip from inadvertent needlesticks. The needle guard having an angled end section configured with a length and a width to retain the needle tip within a tip holding space behind the angled end section.

22 Claims, 8 Drawing Sheets

Related U.S. Application Data

(60) Provisional application No. 61/371,054, filed on Aug. 5, 2010.

(58) Field of Classification Search
CPC .. A61M 2005/3247; A61M 2005/3249; A61M 2005/325
See application file for complete search history.

(56) References Cited

U.S. PATENT DOCUMENTS

| | | | |
|---|---|---|---|
| 5,439,451 | A | 8/1995 | Collinson et al. |
| 6,012,213 | A | 1/2000 | Chang et al. |
| 6,036,171 | A | 3/2000 | Weinheimer et al. |
| 6,203,527 | B1 | 3/2001 | Zadini et al. |
| 6,543,745 | B1 | 4/2003 | Enerson |
| 7,112,191 | B2 | 9/2006 | Daga |
| 7,291,130 | B2 | 11/2007 | McGurk |
| 7,500,965 | B2 | 3/2009 | Menzi et al. |
| 7,608,057 | B2 | 10/2009 | Woehr et al. |
| 7,976,502 | B2 | 7/2011 | Baid |
| 8,162,904 | B2 * | 4/2012 | Takano ............... A61M 5/158 604/263 |
| D672,460 | S | 12/2012 | Baid |
| 8,337,471 | B2 * | 12/2012 | Baid ............... A61M 5/3273 604/263 |
| 8,394,064 | B2 | 3/2013 | Baid |
| 2003/0066978 | A1 | 4/2003 | Enerson |
| 2003/0144627 | A1 | 7/2003 | Woehr et al. |
| 2004/0162525 | A1 | 8/2004 | Vaillancourt et al. |
| 2005/0004532 | A1 | 1/2005 | Woehr et al. |
| 2005/0075609 | A1 | 4/2005 | Latona |
| 2006/0270991 | A1 | 11/2006 | Adams |
| 2009/0054852 | A1 | 2/2009 | Takano et al. |
| 2009/0281499 | A1 | 11/2009 | Harding et al. |
| 2009/0299291 | A1 | 12/2009 | Baid |
| 2010/0191189 | A1 | 7/2010 | Harding et al. |
| 2014/0163470 | A1 * | 6/2014 | Baid ............... A61M 25/0606 604/164.08 |

FOREIGN PATENT DOCUMENTS

| | | |
|---|---|---|
| AU | 2010355003 | 11/2014 |
| AU | 2010299500 | 4/2015 |
| AU | 2011306445 | 5/2016 |
| AU | 2014240216 B2 | 7/2016 |
| CN | 101415456 | 4/2009 |
| CN | 101466431 A | 6/2009 |
| CN | 101743028 A | 6/2010 |
| CN | 102639180 A | 8/2012 |
| EP | 1502621 A2 | 2/2005 |
| EP | 2000165 | 12/2008 |
| EP | 2016963 A1 | 1/2009 |
| EP | 2127692 A1 | 12/2009 |
| EP | 2016963 B1 | 10/2010 |
| EP | 2517751 | 10/2012 |
| EP | 3058976 A1 | 8/2016 |
| IN | 1965/DEL/2009 | 9/2009 |
| RU | 2169585 | 6/2001 |
| RU | 2276611 | 5/2006 |
| RU | 2575312 C2 | 9/2014 |
| VN | 16123 | 10/2016 |
| WO | WO 2005079891 | 9/2005 |
| WO | WO 2009/010847 | 1/2009 |
| WO | WO 2009/020847 | 2/2009 |
| WO | WO 2009116080 | 9/2009 |
| WO | WO-2011036574 A1 * | 3/2011 ........ A61M 25/0618 |
| WO | WO 2011036574 A1 * | 3/2011 ........ A61M 25/0618 |
| WO | WO 2012/016660 | 2/2012 |

OTHER PUBLICATIONS

Examination Report on corresponding foreign application (EP Application No. 16160092.9) from the European Patent Office dated Jan. 17, 2018.

Non-Final Office Action on co-pending U.S. Appl. No. 13/195,492 dated Apr. 7, 2016.

Non-Final Office Action on co-pending U.S. Appl. No. 13/195,492 dated Oct. 1, 2014.

Extended European Search Report from European Patent Office on related EP application (EP16160092.9) dated Jul. 21, 2016.

Search Report & Written Opinion from Intellectual Property Office of Singapore on corresponding SG application (10201503405S) dated Oct. 2, 2015.

Decision on Grant on corresponding foreign application (RU Application No. 2013109410) from the Federal Service on Industrial Property dated Sep. 17, 2015.

Examiner's Report on corresponding foreign application (CN Application No. 201180048319.6) from the State Intellectual Property Office dated Sep. 14, 2015.

Examiner's Report on corresponding foreign application (MY Application No. PI2013700193) from the Malaysian Intellectual Property Office dated Aug. 14, 2015.

Examiner's Report on corresponding foreign application (CN Application No. 201180048319.6) from the State Intellectual Property Office dated Sep. 2, 2014.

Examiner's Report on corresponding foreign application (SG Application No. 201300856-0) from the Intellectual Property Office of Singapore dated Sep. 12, 2013.

In the High Court of Malaya at Kuala Lumpur: Civil Suit Nos. D 22IP-53-2010 and D-22IP-23-2011; Defendant's Written Submissions dated May 15, 2012 (11 pages).

International Preliminary Report on Patentability dated Feb. 5, 2013 from corresponding International Application No. PCT/EP2011/003746 filed Jul. 26, 2011 (7 pages).

International Search Report dated Sep. 28, 2011 from corresponding International Application No. PCT/EP2011/003746 filed Jul. 26, 2011 (4 pages).

Written Opinion dated Sep. 28, 2011 from corresponding International Application No. PCT/EP2011/003746 filed Jul. 26, 2011 (6 pages).

Second Office Action of corresponding foreign application (CN Application No. 201180048319.6) from the State Intellectual Property Office dated Apr. 14, 2015.

Fourth Office Action of corresponding foreign application (CN Application No. 201180048319.6) from the State Intellectual Property Office dated Jan. 29, 2016.

English Translation of First Office Action of corresponding foreign application (CO Application No. 13-34538-6) from the State Intellectual Property Office dated Mar. 11, 2014.

Examiner's Report on corresponding foreign application (EP Application No. 11736297.0) from the European Patent Office dated Jul. 5, 2016.

Office Action of corresponding foreign application (RU Application No. 2013109410) from the Russian Intellectual Property Office dated Jun. 15, 2015.

Invitation to Respond to Written Opinion on corresponding foreign application (SG Application No. 2013008560) from the Intellectual Property Office of Singapore dated Jul. 8, 2014.

Examination Report of corresponding foreign application (SG Application No. 2013008560) from the Intellectual Property Office of Singapore dated Dec. 12, 2014.

Notice of Eligibility for Grant encl. Examination Report of corresponding foreign application (SG Application No. 10201503405S) from the Intellectual Property Office of Singapore dated Jul. 1, 2016.

Examination Report of corresponding foreign application (AU Application No. 2011287917) from the Australian Intellectual Property Office dated Feb. 27, 2014.

Notice of Acceptance of corresponding foreign application (AU Application No. 2011287917) from the Australian Intellectual Property Office dated Jun. 18, 2014.

Statement of Grounds and Particulars—Opposition Procedure of corresponding foreign application (AU Application No. 2011287917); Chrysiliou, Kerry; Oct. 3, 2014.

(Part 1 of 5) Opposition Procedure—Submission of Evidence in Support on corresponding foreign application (AU Application No. 2011287917); Chrysiliou, Kerry; Apr. 7, 2015.

(56) References Cited

OTHER PUBLICATIONS (Part 2 of 5) Opposition Procedure—Submission of Evidence in Support on corresponding foreign application (AU Application No. 2011287917); Chrysiliou, Kerry; Apr. 7, 2015.
(Part 3 of 5) Opposition Procedure—Submission of Evidence in Support on corresponding foreign application (AU Application No. 2011287917); Chrysiliou, Kerry; Apr. 7, 2015.
(Part 4 of 5) Opposition Procedure—Submission of Evidence in Support on corresponding foreign application (AU Application No. 2011287917); Chrysiliou, Kerry; Apr. 7, 2015.
(Part 5 of 5) Opposition Procedure—Submission of Evidence in Support on corresponding foreign application (AU Application No. 2011287917); Chrysiliou, Kerry; Apr. 7, 2015.
Applicant's Written Submissions—Opposition Procedure of corresponding foreign application (AU Application No. 2011287917); B. Braun Melsungen AG; Mar. 15, 2016.
Decision on Patent Opposition of corresponding foreign application (AU Application No. 2011287917) from the Australian Intellectual Property Office dated May 5, 2016.
Examination Report of corresponding foreign application (AU Application No. 2014240216) from the Australian Intellectual Property Office dated May 10, 2016.
Statement of Grounds and Particulars—Opposition Procedure of corresponding foreign application (AU Application No. 2014240216); Chrysiliou, Kerry; Jan. 13, 2017.
Exhibit Pkg-1; Opposition Procedure—Submission of Evidence in Support on corresponding foreign application (AU Application No. 2014240216); Apr. 13, 2017.
Exhibit Pkg-3; Opposition Procedure—Submission of Evidence in Support on corresponding foreign application (AU Application No. 2014240216); Apr. 13, 2017.
Exhibit Pkg-4; Opposition Procedure—Submission of Evidence in Support on corresponding foreign application (AU Application No. 2014240216); Apr. 13, 2017.
Exhibit Pkg-5; Opposition Procedure—Submission of Evidence in Support on corresponding foreign application (AU Application No. 2014240216); Apr. 13, 2017.
(Part 1 of 2) Exhibit Pkg-6; Opposition Procedure—Submission of Evidence in Support on corresponding foreign application (AU Application No. 2014240216); Apr. 13, 2017.
(Part 2 of 2) Exhibit Pkg-6; Opposition Procedure—Submission of Evidence in Support on corresponding foreign application (AU Application No. 2014240216); Apr. 13, 2017.
Exhibit Pkg-7; Opposition Procedure—Submission of Evidence in Support on corresponding foreign application (AU Application No. 2014240216); Apr. 13, 2017.
Exhibit Pkg-8; Opposition Procedure—Submission of Evidence in Support on corresponding foreign application (AU Application No. 2014240216); Apr. 13, 2017.
Exhibit Pkg-10; Opposition Procedure—Submission of Evidence in Support on corresponding foreign application (AU Application No. 2014240216); Apr. 13, 2017.
Exhibit Pkg-12; Opposition Procedure—Submission of Evidence in Support on corresponding foreign application (AU Application No. 2014240216); Apr. 13, 2017.
Exhibit Pkg-18; Opposition Procedure—Submission of Evidence in Support on corresponding foreign application (AU Application No. 2014240216); Apr. 13, 2017.
Exhibit Pkg-19; Opposition Procedure—Submission of Evidence in Support on corresponding foreign application (AU Application No. 2014240216); Apr. 13, 2017.
Exhibit Pkg-21; Opposition Procedure—Submission of Evidence in Support on corresponding foreign application (AU Application No. 2014240216); Apr. 13, 2017.
IN Provisional Patent Appl No. 1965/DEL/2009 dated Sep. 22, 2009; Opposition Procedure—Submission of Evidence in Support on corresponding foreign application (AU Application No. 2014240216); Apr. 13, 2017.
Exhibit JRG-1; Opposition Procedure—Submission of Evidence in Support on corresponding foreign application (AU Application No. 2014240216); Apr. 13, 2017.
Exhibit JRG-3; Opposition Procedure—Submission of Evidence in Support on corresponding foreign application (AU Application No. 2014240216); Apr. 13, 2017.
(Part 1 of 3) Exhibit JRG-6; Opposition Procedure—Submission of Evidence in Support on corresponding foreign application (AU Application No. 2014240216); Apr. 13, 2017.
(Part 2 of 3) Exhibit JRG-6; Opposition Procedure—Submission of Evidence in Support on corresponding foreign application (AU Application No. 2014240216); Apr. 13, 2017.
(Part 3 of 3) Exhibit JRG-6; Opposition Procedure—Submission of Evidence in Support on corresponding foreign application (AU Application No. 2014240216); Apr. 13, 2017.
Exhibit RB-3; Opposition Procedure—Submission of Evidence in Support on corresponding foreign application (AU Application No. 2014240216); Apr. 13, 2017.
Exhibit RB-6; Opposition Procedure—Submission of Evidence in Support on corresponding foreign application (AU Application No. 2014240216); Apr. 13, 2017.
Exhibit RB-11; Opposition Procedure—Submission of Evidence in Support on corresponding foreign application (AU Application No. 2014240216); Apr. 13, 2017.
Exhibit RB-12; Opposition Procedure—Submission of Evidence in Support on corresponding foreign application (AU Application No. 2014240216); Apr. 13, 2017.
Exhibit RB-13; Opposition Procedure—Submission of Evidence in Support on corresponding foreign application (AU Application No. 2014240216); Apr. 13, 2017.
Exhibit RB-14; Opposition Procedure—Submission of Evidence in Support on corresponding foreign application (AU Application No. 2014240216); Apr. 13, 2017.
Exhibit RB-15; Opposition Procedure—Submission of Evidence in Support on corresponding foreign application (AU Application No. 2014240216); Apr. 13, 2017.
Exhibit RB-16; Opposition Procedure—Submission of Evidence in Support on corresponding foreign application (AU Application No. 2014240216); Apr. 13, 2017.
Exhibit RB-20; Opposition Procedure—Submission of Evidence in Support on corresponding foreign application (AU Application No. 2014240216); Apr. 13, 2017.
Exhibit RB-25; Opposition Procedure—Submission of Evidence in Support on corresponding foreign application (AU Application No. 2014240216); Apr. 13, 2017.
Substantive Examination Clear Report on corresponding foreign application (MY Application No. PI2013700193) from the Malaysian Intellectual Property Office dated Sep. 15, 2017.
PRATAP Declaration with Exhibits on related foreign application (AU Application No. 2014240216) in the name of B. Braun Melsungen AG and Opposition by Kerry Chrysiliou dated Sep. 7, 2017, 46 pages.
BAID Declaration with Exhibits on related foreign application (AU Application No. 2014240216) in the name of B. Braun Melsungen AG and Opposition by Kerry Chrysiliou dated Sep. 15, 2017, 538 pages.
Opposition Decision on corresponding foreign application (AU Application No. 2014240216) from the Australian Patent Office dated May 30, 2018.
Office Action on corresponding foreign application (EP Application No. 16160092.9) from the European Patent Office dated Jul. 11, 2018.
Office Action on corresponding foreign application (CN Application No. 201610892436.5) from the National Intellectual Property Administration, P.R. China dated Apr. 24, 2019.
Office Action on corresponding foreign application (EP Application No. 11736297.0) from the European Patent Office dated Aug. 3, 2018.
Substantive Examination Adverse Report on corresponding foreign application (MY Application No. PI 2015001799) from the Intellectual Property Corporation of Malaysia dated Apr. 2, 2019.

(56) References Cited

OTHER PUBLICATIONS

First Examination Report (FER) on corresponding foreign application (IN Application No. 1062/DELNP/2013) from the Indian Patent Office dated Jul. 26, 2019.
Office Action on corresponding foreign application (RU Application No. 2016101256) from the Russian Patent Office dated Jun. 27, 2019.
Opposition, submitted by Aliat Legal for Poly Medicare Limited to the Intellectual Property Office of Vietnam, on corresponding foreign application (VN Application No. 1-2016-02159), Opposition No. PD1-2018-00792, dated Jul. 27, 2017.
Office Action on corresponding foreign application (VN Application No. 1-2016-02159) from the Intellectual Property Office of Vietnam dated Sep. 12, 2019.
Final Office Action on related U.S. Appl. No. 13/195,492 dated Apr. 10, 2015.
Final Office Action on related U.S. Appl. No. 13/195,492 dated Nov. 2, 2016.
Non-Final Office Action on co-pending U.S. Appl. No. 16/539,887 dated Oct. 1, 2019.
Notice of Filing of Sep. 4, 2013, AU Affidavit of Michelle Di Sciascio, Federal Court of Australia, (No. VID463/2013) dated Sep. 3, 2013, 17 pages.
Notice of Filing of Oct. 29, 2013, AU Second Affidavit of Michelle Di Sciascio, Federal Court of Australia, (No. VID463/2013) dated Oct. 29, 2013, 3 pages.
Michelle Di Sciascio, AU Declaration, in the matter of patent application No. 2011287917, in the name of B Braun Melsungen AG and Opposition by Kerry Chrysiliou, dated Apr. 2, 2015, 8 pages.
AU Declaration of Girdhari Lal Sharma to IP Australia in AU Opposition Procedure Application No. 2011287917, in the name of B. Braun Melsungen AG, Opposition by Kerry Chrysiliou, dated Sep. 10, 2015, 15 pages.
AU Third Declaration of Kerry Chysiliou to IP Australia in AU Opposition Procedure Application No. 2011287917, in the name of B. Braun Melsungen AG, Opposition by Kerry Chrysiliou, dated Sep. 14, 2015, 178 pages.
AU Fourth Declaration of Kerry Chysiliou to IP Australia in AU Opposition Procedure Application No. 2011287917, in the name of B. Braun Melsungen AG, Opposition by Kerry Chrysiliou, dated Sep. 14, 2015, 90 pages.
Evidence in Reply to IP Australia in AU Opposition Procedure Application No. 2011287917, in the name of B. Braun Melsungen AG, Opposition by Kerry Chrysiliou, dated Sep. 14, 2015, 1 page.
Patent Oppositions—Acknowledge EIR, Request Hearing Dates on corresponding foreign application (AU Application No. 2011287917) from IP Australia dated Sep. 15, 2015.
Notice of Acceptance on corresponding foreign application (AU Application No. 2014240216) from IP Australia dated Jul. 1, 2016.
Opponent's Letter Enclosing Amended Statement of Grounds and Particulars to IP Australia, Opposition to AU Application No. 2014240216, dated Jun. 22, 2017, 20 pages.
Opposition—Statement of Grounds and Particulars on corresponding foreign application (AU Application No. 2014240216) from IP Australia dated Jun. 26, 2017.
Evidence in Answer on corresponding AU Application No. 2014240216 to IP Australia dated Jul. 18, 2017, 119 pages.
(Part 1 of 7) AU Affidavit of Rishi Baid, Federal Court of Australia, (No. VID740/2018) dated Nov. 24, 2018, 127pages.
(Part 2 of 7) AU Affidavit of Rishi Baid, Federal Court of Australia, (No. VID740/2018) dated Nov. 24, 2018, 64 pages.
(Part 3 of 7) AU Affidavit of Rishi Baid, Federal Court of Australia, (No. VID740/2018) dated Nov. 24, 2018, 60 pages.
(Part 4 of 7) AU Affidavit of Rishi Baid, Federal Court of Australia, (No. VID740/2018) dated Nov. 24, 2018, 79 pages.
(Part 5 of 7) AU Affidavit of Rishi Baid, Federal Court of Australia, (No. VID740/2018) dated Nov. 24, 2018, 60 pages.
(Part 6 of 7) AU Affidavit of Rishi Baid, Federal Court of Australia, (No. VID740/2018) dated Nov. 24, 2018, 57 pages.
(Part 7 of 7) AU Affidavit of Rishi Baid, Federal Court of Australia, (No. VID740/2018) dated Nov. 24, 2018, 64 pages.
AU Affidavit of Prabhakar Mani Pratap, Federal Court of Australia, (No. VID740/2018) dated Nov. 24, 2018, 102 pages.
(Part 1 of 3) AU Affidavit of Ernesto Hueso, Federal Court of Australia, (No. VID740/2018) dated Nov. 27, 2018, 116 pages.
(Part 2 of 3) AU Affidavit of Ernesto Hueso, Federal Court of Australia, (No. VID740/2018) dated Nov. 27, 2018, 30 pages.
(Part 3 of 3) AU Affidavit of Ernesto Hueso, Federal Court of Australia, (No. VID740/2018) dated Nov. 27, 2018, 65 pages.
AU Affidavit of Emma Kate Mitchell, Federal Court of Australia, (No. VID740/2018) dated Nov. 27, 2018, 8 pages.
AU Affidavit of Leanne Michelle Oitmaa, Federal Court of Australia, (No. VID740/2018) dated Nov. 27, 2018, 7 pages.
Notice of Filing of Dec. 7, 2018, AU Affidavit of Peter Cox, Federal Court of Australia, (No. VID740/2018) dated Dec. 7, 2018, 8 pages.
Notice of Filing of Mar. 8, 2019, AU Affidavit of William Samuel Hunter, Federal Court of Australia, (No. VID740/2018) dated Mar. 8, 2019, 197 pages.
Notice of Filing of Mar. 22, 2019, AU Affidavit of Essenese Obhan, Federal Court of Australia, (No. VID740/2018) dated Mar. 20, 2019, 230 pages.
Peter Cox, Measurement Report on Multigate Safety I.V. Cannula, Lot No. 3105009L, Australian Government Department of Industry, Innovation and Science, National Measurement Institute, West Lindfield, Australia, Ref: RN190613, File: CB/18/0258, dated Mar. 20, 2019.
(Part 1 of 2) Notice of Filing of Jun. 7, 2019, AU Affidavit of Prabhakar Mani Pratap, Federal Court of Australia, (No. VID740/2018) dated Jun. 6, 2019, 60 pages.
(Part 2 of 2) Notice of Filing of Jun. 7, 2019, AU Affidavit of Prabhakar Mani Pratap, Federal Court of Australia, (No. VID740/2018) dated Jun. 6, 2019, 81 pages.
Notice of Filing of Jun. 7, 2019, AU Second Affidavit of Rishi Baid, Federal Court of Australia, (No. VID740/2018) dated Jun. 7, 2019, 132 pages.
Office Action on corresponding foreign application (BR Application No. 112013002767-3) from the Brazilian Patent and Trademark Office dated Oct. 22, 2019.
EP2600925 (European parent patent application No. 11736297.0), 28 pages.
EP3058976B1, the opposed divisional patent application based on EP 11736297.0 (EP2600925) as originally filed, received by the EPO on Mar. 14, 2016, 32 pages.
Communication under Rule 71(3) EPC on corresponding foreign application (EP Application No. 16 160 092.9) from the European Patent Office dated Feb. 20, 2019.
Notice of Opposition on corresponding foreign application (EP Application No. 16 160 092.9) from the European Patent Office dated Oct. 10, 2019, 67 pages.
High Resolution Drawings of document D6, EP Opposition against EP 3058976, dated Oct. 18, 2019, 9 pages.
Office Action on corresponding foreign application (EP Application No. 11 736 297.0) from the European Patent Office dated Dec. 4, 2019.
IN Affidavit of Kevin Woehr, in the High Court at New Delhi, (CS (OS) No. 186 of 2008) dated Oct. 26, 2010, 20 pages.
Priority Document U.S. Appl. No. 61/371,054, filed Aug. 5, 2010.
Notification of Defects on corresponding foreign application (VN Application No. 1-2013-00690) from the Ministry of Science and Technology National Office of Intellectual Property Socialist Republic of Vietnam dated May 16, 2016.
Feature Analysis of Claim1 of EP 3058976 B1, Oct. 10, 2019, 1 page.
Photographs of Medica Sample of Polysafety as filed with Kevin Woehr's affidavit, 8 pages.

* cited by examiner

NEEDLE SAFETY DEVICE AND ASSEMBLY

CROSS-REFERENCE TO RELATED APPLICATION

This is a continuation of Ser. No. 13/195,492, filed Aug. 1, 2011, which is a regular utility application of U.S. Provisional Application No. 61/371,054, filed Aug. 5, 2010, the contents of which are expressly incorporated herein by reference.

BACKGROUND

The disclosure generally relates to needle safety assemblies and safety intravenous catheters (IVCs), and, in particular, to a safety IVC in which the needle tip is automatically covered after needle withdrawal to prevent unintended needlestick with the needle tip.

DESCRIPTION OF RELATED ART

Intravenous catheters are primarily used to administer fluids directly into a patient's vascular system. Typically, a catheter is inserted into a patient's vein by a health care worker. Immediately after the withdrawal of the needle from the patient's vein, the exposed needle tip creates a danger of an accidental needlestick occurring, which leaves the health care worker vulnerable to the transmission of various dangerous blood-borne pathogens.

This danger has led to the development of safety IVCs that cover or hide the needle tip using several different means. However, some safety IVCs that have been developed sometimes fail to prevent unintended needlesticks from occurring. For example, in some safety IVCs, the turning of the needle during removal may cause the needle tip to slide out from within the confines of the needle guard.

In some safety IVCs, the engagement that typically occurs between the needle and the needle guard during withdrawal of the needle is unreliable.

SUMMARY

The various embodiments of the present safety IVC have several features, no single one of which is solely responsible for their desirable attributes. The prominent features of these embodiments will now be discussed briefly without any intention of limiting the scope of the embodiments expressed herein.

In certain embodiments, a needle guard comprising a non-metallic base portion comprising a bore, a proximally facing surface, and a distally facing surface are incorporated. The guard further includes a first arm including a first free end and a second arm including a second free end extending generally axially from the base portion in a distal direction. The first free end extending beyond the second free end and including an angled end section that extends toward the second arm. Wherein the angled distal end section comprises a length and a width configured to retain a needle having a needle diameter within a tip holding space and wherein the length and width of the angled distal end section are larger than the needle diameter.

In other embodiments, a catheter assembly comprising a needle guard comprising: a non-metallic base portion comprising a bore, a proximally facing surface, and a distally facing surface is provided. The guard includes a first arm including a first free end and a second arm including a second free end extending generally axially in a distal direction from the base portion. The first free end extend beyond the second free end and including an angled end section comprising a length and a width that extends toward the second arm and a needle having a diameter. Wherein the first arm and the second arm are biased so as to move between a ready position in which the angled end section abuts a needle having a needle tip and a protected position in which the needle tip is confined within a tip holding space. Wherein the length and width of the angled distal end section are larger than the needle diameter.

In yet another embodiment, a safety IVC comprising a needle hub with a needle and a catheter hub with a catheter tube and a tip protector is provided. The tip protector is made from a first material and having a proximal wall comprising an opening defining a bore and two arms extending distally of the proximal wall with at least one of the arms comprising an angled end section configured for covering a distal end of the other arm in a protective position. Wherein an insert made from a second material comprising an opening is aligned with the opening of the proximal wall and wherein the opening of the proximal wall requires less force to enlarge than the opening of the insert.

Another embodiment of the present assembly includes a needle assembly comprising a non-metallic base portion comprising wall having a bore, a bore length, a bore diameter, a proximally facing surface, and a distally facing surface. The guard further includes a first arm including a first free end and a second arm including a second free end extending generally axially in a distal direction from the base portion, the first free end extending beyond the second free end and including an angled end section comprising a first side edge, a second side edge, a length, and a width that extends toward the second arm. The guard includes a needle tip holding space defined at least in part by the base portion, the first arm, the second arm, and the angled end section. The assembly further includes a needle having a tip and a diameter. Wherein the first arm and the second arm are biased so as to move between a ready position in which the angled end section abuts the needle and a protected position in which the needle tip is confined within a tip holding space and wherein the length and width of the angled distal end section are larger than the needle diameter and cooperate with the bore length and bore diameter to confine the needle tip within the needle tip holding space.

A still further feature of the present application is a method for assembling a needle assembly. The method comprising providing a needle having a needle shaft, a needle tip, and a change in profile near the needle tip on a needle hub and placing a needle guard slidably about the needle shaft. The needle guard comprising a non-metallic base portion comprising wall having a bore, a bore length, a bore diameter, a proximally facing surface, and a distally facing surface. The needle guard further comprising a first arm including a first free end and a second arm including a second free end extending generally axially in a distal direction from the base portion, the first free end extending beyond the second free end and including an angled end section comprising a first side edge, a second side edge, a length, and a width that extends toward the second arm. The needle guard further comprising a needle tip holding space defined at least in part by the base portion, the first arm, the second arm, and the angled end section. Wherein the length and width of the angled distal end section are larger than a needle diameter and cooperate with the bore length and bore diameter to confine the needle tip within the needle tip holding space. The method further comprising moving the needle guard to a proximal position on the needle shaft so that the angled end section is based by the needle shaft and is spaced from the needle tip.

BRIEF DESCRIPTION OF THE DRAWINGS

The various embodiments of the present needle assemblies and safety IVCs now will be discussed with an emphasis on highlighting the advantageous features. These embodiments depict the novel and non-obvious safety IVC shown in the accompanying drawings, which are for illustrative purposes only. These drawings include the following figures, in which like numerals indicate like parts.

DETAILED DESCRIPTION

The detailed description set forth below in connection with the appended drawings is intended as a description of the presently preferred embodiments of safety IVCs provided in accordance with the present apparatus, system and method and is not intended to represent the only forms in which the present apparatus, system and method may be constructed or utilized. The description sets forth the features and the steps for constructing and using the safety IVCs of the present apparatus, system and method in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

The figures and their written descriptions indicate that certain components of the embodiments are formed integrally and certain other components are formed as separate pieces. Those of ordinary skill in the art will appreciate that those components shown and described herein as being formed integrally, in the alternative, may be formed as separate pieces. Those of ordinary skill in the art will further appreciate that components shown and described herein as being formed as separate pieces may in alternative embodiments be formed integrally. Further, as used herein the term integral describes a single piece, which may be singularly formed or singularly embodied whereas unitary means monolithically formed.

Figure 1:
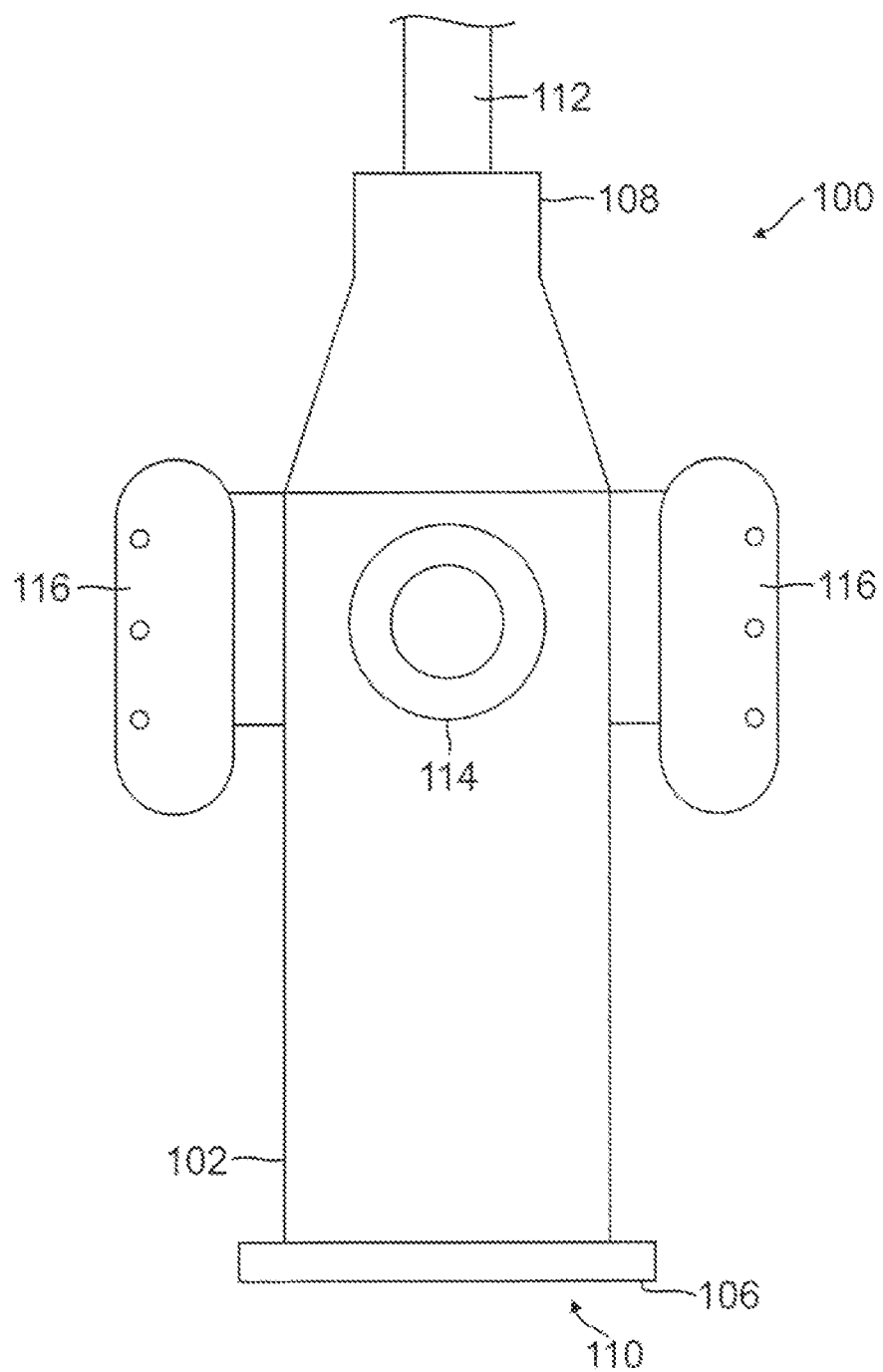
FIG. 1 is a top view of a safety catheter hub having wings in accordance with an embodiment.

FIG. 1 is an illustration of a catheter housing 100 in accordance with an embodiment. The catheter housing 100 includes a catheter hub body 102. The hub body or catheter hub 102 defines an internal chamber 104 (FIG. 2) extending between a proximal end 106 and a distal end 108 of the hub body 102. A hollow catheter tube 112 is affixed at the distal end 108 of the hub body 102 using a bush or retainer 203 (FIG. 2), which is known in the industry. An axial or proximal opening 110 is defined at the proximal end 106 of the hub body 102. The axial opening 110 is configured to receive a hollow needle hub, which includes a needle on its distal end and a flash chamber at its proximal end. The axial opening 110 may embody a female Luer taper, which is typical in the industry. Alternatively, the needle hub abuts the end of the proximal end 106 but not enter the internal chamber 104. As used herein, the term distal end or proximal end means an end in a distal general location or proximal general location, respectively, or distal most end or proximal most end, respectively. If only a distal most end or a proximal most end is intended, the text will so indicate.

In some embodiments, the hub body 102 includes a port 114, which extends from the hub body 102 in a direction generally perpendicular to the axial direction of the internal chamber 104. In another embodiment, the port 114 is not included. In still yet another embodiment, the port comprises a valve or a piston for regulating fluid flow through the opening of the port 114. For example, the port 114 and the valve may embody a needleless access valve. Exemplary needleless access valves are disclosed in U.S. Pat. Nos. 5,439,451; 6,036,171; and 6,543,745, the contents of each of which are expressly incorporated herein by reference. Alternatively or in addition thereto, a plastic or elastomeric sleeve 82 (FIG. 2) may be used to control flow through the port 114, which is well known in the industry. The sleeve 82 is configured to collapse upon application of fluid pressure caused by, for example, a syringe. In some embodiments, wings 116 may be provided on the hub body 102. The wings 116 may be positioned to extend out from the hub body in a plane perpendicular to the port 114, when the port 114 is positioned on the hub body 102.

Figure 2:
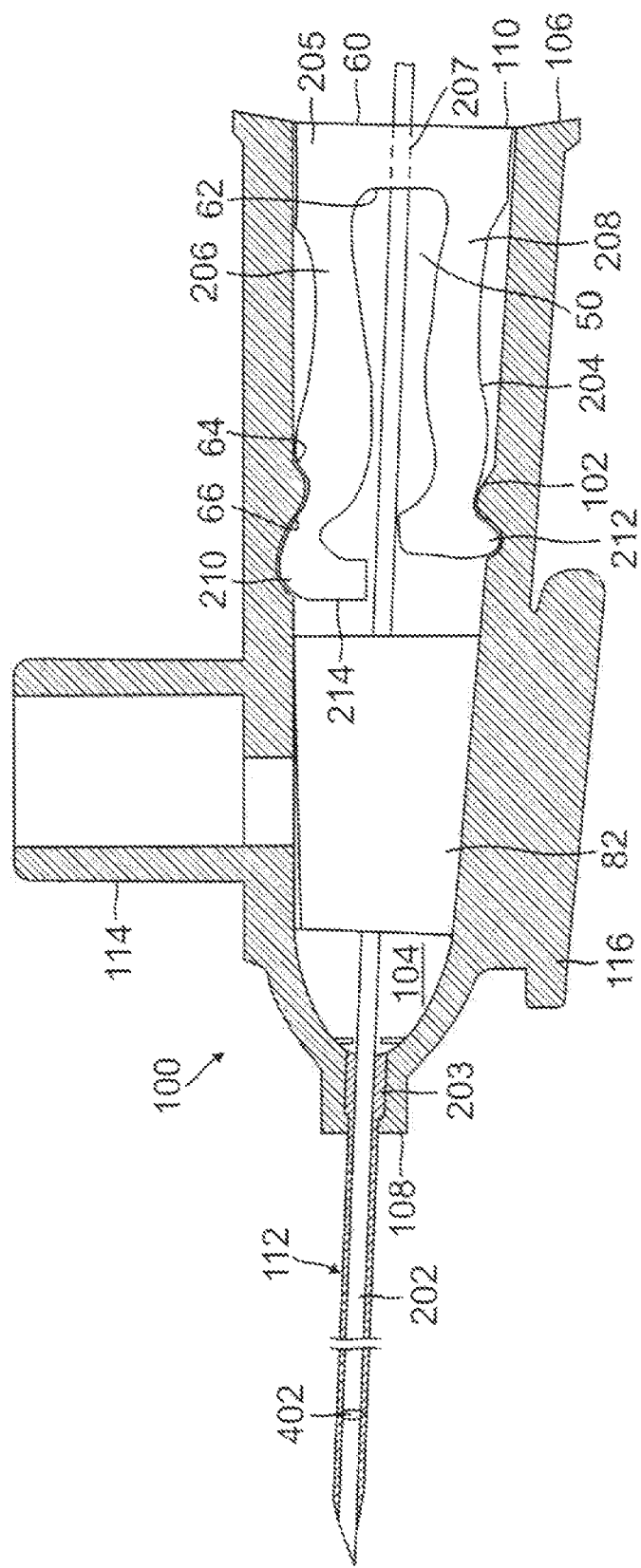
FIG. 2 is a cross-sectional view of the safety catheter hub of FIG. 1 including a needle in accordance with an embodiment.

FIG. 2 is a cross-sectional view of the safety catheter hub 100 of FIG. 1 in accordance with an embodiment. Generally, as shown in FIG. 2, a needle 202 is received through the axial opening 110 and extends through the internal chamber 104. At the distal end 108 of the hub body 102, the needle 202 extends into and through the tubular catheter 112 and the needle tip extends beyond the distal end of the tubular catheter 112.

In one embodiment, a protective needle guard 204 is incorporated and slidably arranged on the needle 202. The needle guard 204 includes a base portion 205, which defines a bore 207 extending axially therethrough for receiving the needle 202. As described in greater detail below, the bore 207 is configured in size and shape to allow the needle 202 to be slidably received therein. The needle guard 204 also includes a first arm 206 and a second arm 208, which extend generally axially from the base portion 205.

Figure 3A:
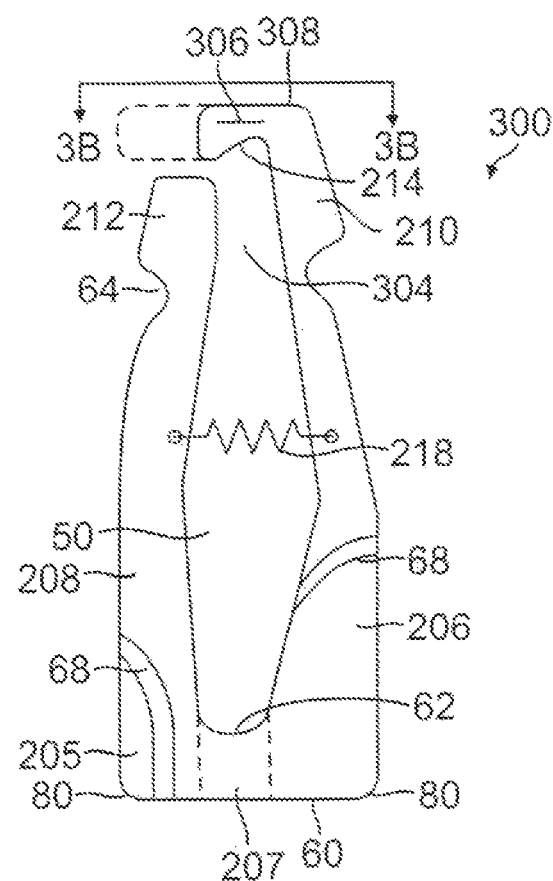
FIG. 3A is a side view of a needle guard in accordance with various embodiments.

The base portion 205 further comprises a wall comprising proximally facing wall surfaces 60 and distally facing wall surfaces 62 (See also FIG. 3A). A gap 50 is provided between the two arms 206, 208, which are defined by the edges of the two arms and the distally facing wall surfaces 62 of the base portion 205. The first arm 206 has a first free or cantilevered end 210 and the second arm 208 has a second free or cantilevered end 212. The first free end 210 extends beyond the second free end 212 and has an angled end section 214, which may be referred to as a wall, a protective section, a blocking tip, or a cap. The angled end section 214 extends towards the second arm 208. In the embodiment shown, the angled end section 214, the first arm 206, and the base portion 205 are formed contiguously or unitarily with one another. Also, as used herein, the term first and second are merely identifiers and do not necessarily limit the physical features of the arms. For example, when viewed from another perspective, the first arm may be called the second arm and vice-versa.

In one embodiment, the needle guard 204 is made from a unitary plastic, a thermoplastic, or an elastomer material or any combination thereof, such as a thermoplastic elastomer (TPE). For example, the needle guard 204 may be made from shaped memory elastomer so that the first arm 206 self-biases towards the second arm and the angled end section 214 overlaps the end of the second arm, at least partially. Use of shaped memory or resilient material permits the needle guard 204 to self-bias to a closed or protective position without external biasing forces, as further discussed below. More particularly, the first arm 206, the second arm 208 or both the first arm and the second arm are configured to pivot radially inwardly to cover the needle tip with use of shaped memory plastic or elastic material. Upon movement of the arm, the gap 50 provided between the two arms is reduced. In other embodiments, the needle guard 204 is made from multi-pieces and/or made from a combination of different materials, such as plastic and metal, e.g., polycarbonate and stainless steel.

In the ready position of the safety catheter hub 100 shown in FIG. 2, the needle guard 204 is located at the proximal end 106 of the catheter hub 102. As shown, the needle guard is located substantially in the interior of the internal chamber 104. It can also be wholly located in the interior chamber 104 or partially located outside of the axial opening 110. The needle 202 extends through the bore of the needle guard 204 and into the internal chamber 104. The needle extends distally through the catheter 112 so that the tip of the needle 202 extends beyond the distal end of the catheter tube 112. In the ready position, when the needle 202 extends through the needle guard 204, the angled end section 214 is supported on the needle 202, such as contacted or abutted by the needle, which causes the first free end 210 of the first arm 206 to be forced or biased away from the second free end 212 of the second arm 208. As shown, the cantilevered end 212 of the second arm 208 is also biased by the needle in the ready position.

To axially locate the needle guard 204 within the catheter hub 102 in the ready position and during transition from the ready position to a used position, the needle guard incorporates a hub engaging section 64 and the hub 102 incorporates a guard engaging section 66. As shown, the hub engaging section 64 is a groove and the guard engaging section 66 is a projection that projects from the interior wall surface of the hub 102. In another embodiment, the configuration is reversed so that the hub engaging section 64 is a projection and the guard engaging section 66 is a groove. In one embodiment, the engagement is not circumferential but only partly around the needle guard so that only one of the arms is engaged to the hub. In another embodiment, the engagement is circumferential around the needle guard. As shown, the hub 102 incorporates both a recess and a projection. In another embodiment, the hub incorporates a projection to form an interior cavity of reduced diameter but not a recess. When the angled end section 214 of the guard is in contact with the needle in the ready position, the needle pushes the angled end section radially outwardly relative to the needle shaft so that the hub engaging section 64 engages the guard engaging section 66 to retain the guard within the interior cavity of the hub 102.

Figure 2A:
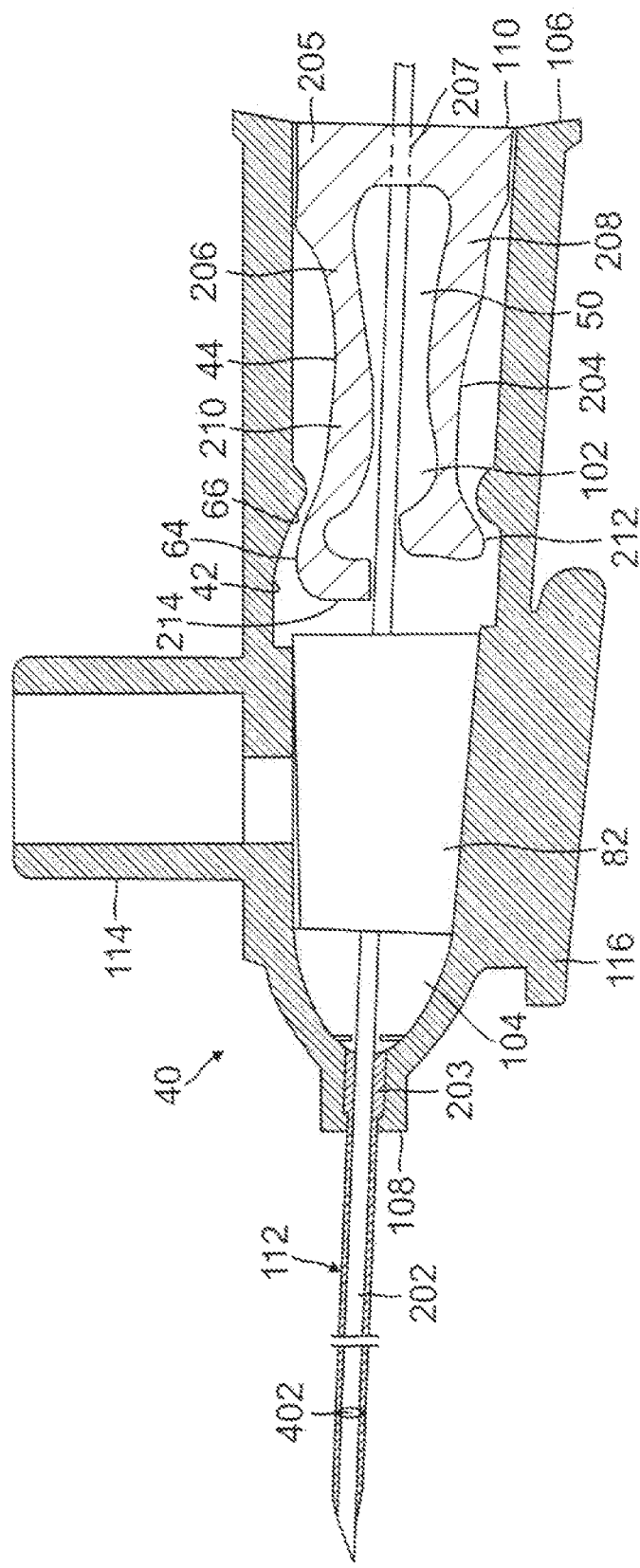
FIG. 2A is a cross-sectional view of a modified safety catheter assembly provided in accordance with an embodiment.

FIG. 2A is a cross-sectional side view of a safety IVC 40 provided in accordance with an embodiment of the present device and method. The safety IVC 40 is similar to the safety IVC 100 of FIG. 2 with some exceptions. Among other things, the interior cavity of the catheter hub 104 has been modified to include an enlarged groove or recess 42 just distal of the guard engaging section 66. This enlarged groove 42 is configured to accommodate the arcuate hub engaging section 64 on the needle guard 44. As shown, when the needle guard 44 is in the ready position, the guard engaging section 66 is spaced from the hub engaging section 64. However, when the needle 202 is retracted away from the catheter hub, such as after successful venipuncture, the needle guard 44 moves relative to the catheter hub so that the hub engaging section 64 abuts or engages the guard engaging section 66 by the relative movement. The engagement continues until the needle tip moves proximally of the angled end section of both first and second arms. At this point, the first arm 206 and the second arm 208 move radially inwardly to close over the needle tip. Thus, a feature of the present embodiment is a guard having a hub engaging section that is spaced from the catheter hub in a ready position and only engages or abuts the catheter hub upon relative movement.

If the proximal end of the needle guard 204 is flush with the proximal end 106 of the catheter hub 102, or projects outwardly from the proximal end of the catheter hub 102, the needle hub (not shown) may be assembled to the catheter hub by providing a shroud on the needle hub to fit over the catheter hub. In an alternative configuration, the needle guard 204 is recessed inside the catheter hub and a space is provided for a distal end section of the needle hub to fit inside the proximal end of the catheter hub.

In one embodiment, if shaped memory elastomer or non-metallic material without self-biasing is used, the arms 206, 208 may be biased together using any form of tensioning. In other embodiments, a combination of tensioning means and self-biasing non-metallic material is used. As illustrated schematically in FIG. 3A, a tensioning member 218 may be deployed in a region of the needle guard 204 between the base portion 205 or proximal wall and the first and second free ends 210 and 212. In one embodiment, the tensioning member 218 may be a ring made from an elastic material, such as rubber material, silicone or the like, that is made to fit around the first and second arms 206 and 208. The ring exerts a restoring force on the arms, when the arms are spread apart by the needle 202, as in the ready position. In one embodiment, the tensioning member 218 may be a spring, such as a helical coil spring, a leaf spring or other similarly functioning types of springs. In one embodiment, the tensioning member 218 may not be a separate component of the needle guard 204. In this embodiment, one or both of the arms 206 and 208 may be made of a material that has inherent spring-like properties. The inherent spring-like properties cause an inherent restoring force to be stored in the arms when the arms are spread apart by the needle 202 as when in the ready position. Once the needle 202 is removed from contact with the first arm 206, the arms naturally return to the protected position. One or more chamfered surfaces 80 and one or more surface features 68, such as indentations or grooves, may be incorporated for aesthetic appeal and/or to facilitate further resiliency to promote installation. In other embodiments, undercuts or other surface features may be added to facilitate assembly of the tensioning member 218. In one embodiment, a helical spring is fitted over the entire needle guard so that axial force from the spring expansion forces the two arms to move radially inwardly.

In operation, the distal tip of the needle 202 and the catheter tube 112 are inserted into a patient's vein to establish venipuncture. Thereafter, the health care practitioner manually withdraws the needle 202 from the catheter hub 102. A male luer of an intravenous (IV) line attached to the catheter hub may then be fitted with a source of a fluid that is to be administered into the patient's vein.

As the needle 202 is withdrawn from the patient following successful venipuncture, the needle slides proximally relative to the catheter tube while maintaining contact with the angled end section 214 of the needle guard to removably secure the guard to the hub. Once the needle tip moves proximally of the angled end section 214 of the guard, the first arm 206, which is now no longer forced outwardly by the needle, moves radially inwardly to separate the hub engaging section 64 from the guard engaging section 66 to cover the needle tip with the angled end section 214. Further proximal movement of the needle causes a change in profile 402 (FIG. 2) located on the needle shaft to abut the opening 207 on the proximal wall of the guard to stop relative movement between the needle guard and the needle. At that point, the needle guard may be from the catheter hub due to the abutment between the change in profile and the opening on the needle guard. Causing the needle guard to separate from the needle hub to protect the needle tip is further discussed below.

It should be understood that the general configuration and operation of the safety catheter hub 100 thus described provides a context in which the following embodiments of the needle guard may be used to ensure proper and adequate protection to health care practitioners using the safety catheter hub 100. It should further be understood that each of the embodiments described herein may be used separately or in combination with one another, as appropriate and as desired, such as where the functions or features are compatible.

Referring again to FIG. 3A, in an embodiment of a needle guard 300, the length of the angled end section 214 may be designated by the variable Ln, wherein n is a whole integer, such as 1, 2, 3, and so forth. The width (height) of the angled end section 214 may be designated by the variable W, which is more clearly shown in end-view 3B-3B. In one embodiment, the length Ln and width W are selected so that the angled end section 214 is configured to adequately block the needle tip when the needle guard is in the protected position. In one particular embodiment, the length Ln and the width W of the guard are selected so that the tip is blocked or covered by the end section 214, even when the needle is rotated so the point of the bevel still faces the end section 214 or when the needle pivots side-to-side when in the protected position. In addition, the width W and the length Ln are to be wide enough to prevent the needle bevel from contacting an edge of the angled end section 214 since some plastics such as polycarbonate or ABS can be chipped when struck by the needle bevel. Thus, a feature of the present device, assembly, and method is a needle guard having a non-metallic base portion or proximal wall comprising a bore, a proximally facing surface, and a distally facing surface, and wherein the bore and the base portion can be distorted by pivoting the needle but wherein such pivoting does not cause the needle tip to escape from the confines of an angled distal end section due to the length and width of the angled distal end section. In one example, the length is about the same dimension as the width W for a wide needle guard. In another example, the length is about 1.3 or more times greater than the width W, such as 2×, 3×, or 4× greater than the width W. Compared to the diameter of the needle, the width W is preferably 1.25× or greater than the diameter of the needle, such as 2.5×, 3×, or greater than the diameter of the needle.

In one embodiment, the length $L_1$ is selected such that the angled end section 214 protrudes over at least a portion of the second free end 212 when the first and second arms 206 and 208 are in the protected position. Alternatively, the length $L_2$ may be selected such that the angled end section 214 protrudes over between at least a portion of the second free end 212 to over the entire second free end 212 when the first and second arms 206 and 208 are in the protected position. In another alternative embodiment, the length $L_2$ may be selected such that the angled end section 214 protrudes entirely over and beyond the second free end 212 when the first and second arms 206 and 208 are in the protected position. Thus, for example, the length Ln may be selected to cause the angled end section 214 to protrude over a fraction of the second free end 212, between over a fraction to 100% of the second free end 212 or over 100% of the second free end 212 when the first and second arms 206 and 208 are in the protected position.

Figure 3B:
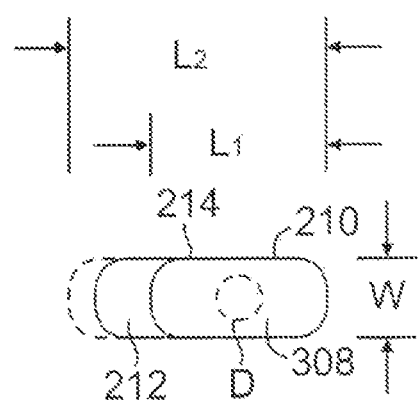
FIG. 3B is an end view of the needle guard of FIG. 3A taken along line 3B-3B.
Figure 3C:
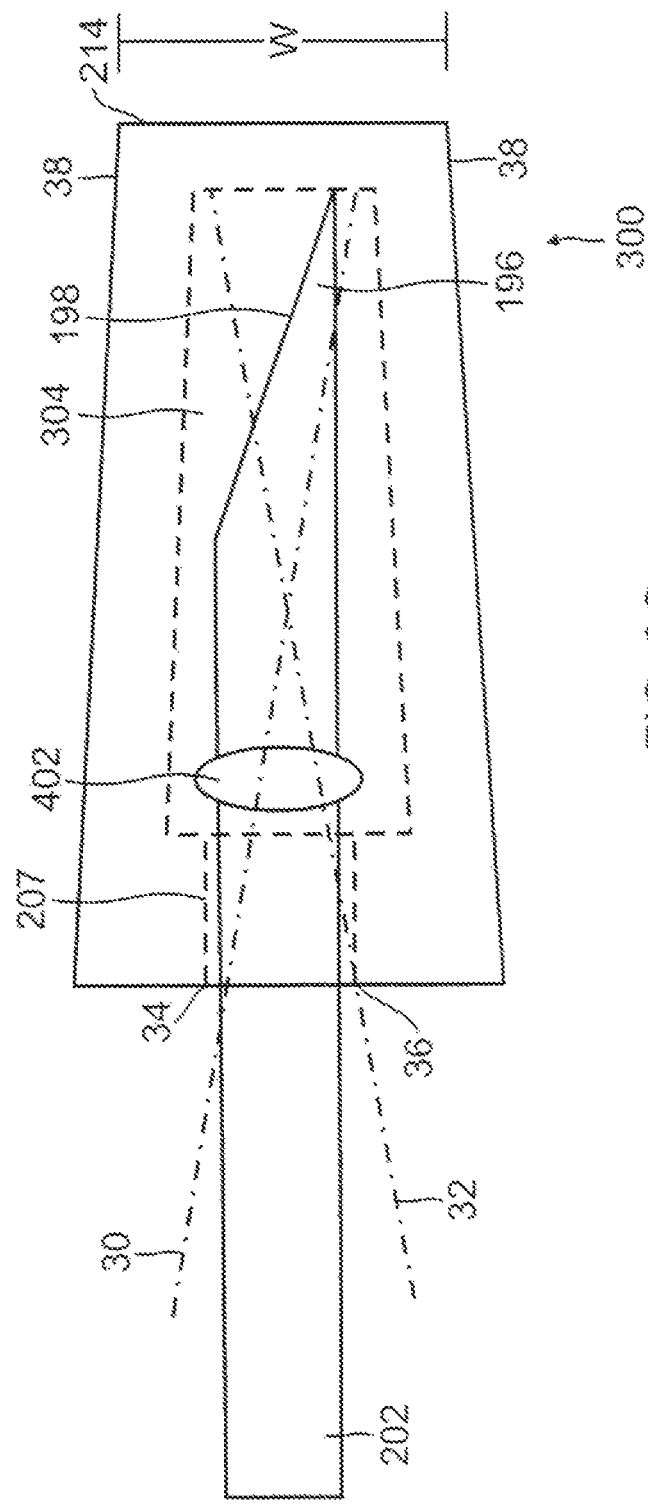
FIG. 3C is a schematic top or plan view of the needle guard of FIG. 3A depicting relationships between the FIG. 4A is a side view of a needle guard in a protected position in accordance with various embodiments and FIG. 4B is a sectional view of the needle guard of FIG. 4A.

Similarly, the width W of the angled end section 214 may be selected such that the angled end section 214 is greater in width W than the width of the second free end 212 when the first and second arms 206 and 208 are in the protected position. Thus, for example, the width W may be selected to be greater than the width of the second free end 212 between a fraction of to about 50% greater than the width of the second free end 212 when the first and second arms 206 and 208 are in the protected position. It should be understood that the selection of the length Ln and the width W may be made independent of the selection of the other dimensions. As shown in FIG. 3B, the width W and the length Ln are always larger than the outside diameter D of the needle 202, so that no matter how the needle is rotated or pivoted in the bore 207 during withdrawal, the needle tip and the bevel are always blocked by the angled end section 214. Thus, the angled end section 214, when in the protected position, creates a space there behind, which is defined by a length and a width of the angled distal end section 214 being greater than the outside diameter D of the needle. In one embodiment, the width is at least 125% greater than the diameter of the needle and the length is at least 200% greater than the diameter of the needle. In other embodiments, the width is from about 150% to about 300% greater than the diameter of the needle. The disclosed length and width along with the bore 207 at the proximal end are configured to retain the needle tip within the open area 304 within the needle guard.

To further facilitate protection of the needle tip, the angled end section 214 of the needle guard may incorporate a shield member or insert 306. The shield member 306 may be made of a puncture resistant material, such as a metal insert or a hard plastic insert. The shield member 306 resists puncturing of the angled end section 214 by the needle tip once the needle has been captured by the needle guard 300. For example, when the guard is made from an elastomer material, the shield member 306 may be incorporated, such as by co-molding or insert molding, to prevent exposure of the needle tip penetrating through the angled end section 214. In another embodiment, the shield member 306 is positioned on an external surface of the angled end section 214, for example on the distal surface 308 or the proximal surface 310 of the angled end section. The shield member 306 may be mounted to the external surface using any well-known means of bonding components together, such as gluing, welding and the like.

FIG. 3B is a schematic top or plan view of the needle guard 300 in a shielded or protected position, which captures the needle tip 196 within the open area 304 of the needle guard. As the needle guard 300 is made, at least in-part, from a non-metallic material that has a lower strength and hardness than a metallic material, the needle can pivot along a first angle, as shown by dashed-dot line 30, or along a second angle, as shown by dashed-dot line 32. In pivoting, the needle can abut the bore 207 at points 34 and 36 and/or corresponding points at the distal edge of the bore 207 and possibly compress or distort part of the bore to further pivot. When this happens, the needle tip 196 moves within the confined open space or needle tip holding space 304 and can slip pass the side edges 38 of the needle guard, near the angled end section 214. However, as discussed above, by selecting an appropriate width W and length ratio, the needle tip is prevented from slipping pass the side edges 38. Alternatively or additionally, the bore 207 inside diameter may be made to have a close fit ratio versus the outside diameter of the needle shaft to minimize the amount of possible pivoting. The bore length can also be utilized in combination with the bore diameter to minimize the amount of possible pivoting. Still furthermore, a relatively harder insert may be incorporated with the bore 207 or inside the bore 207 to not only increase the separation force of the needle, as further discussed below, but to also minimize the amount of possible needle pivoting.

Figure 4A:
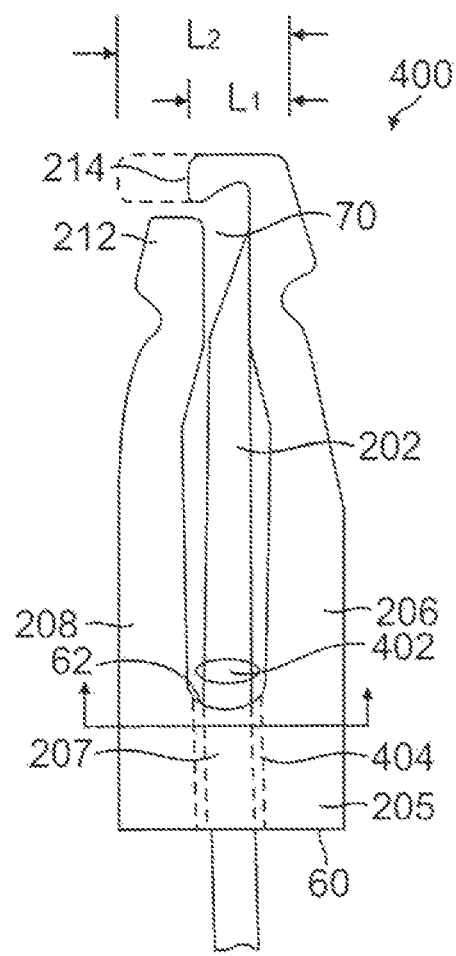
FIG. 4C is a side view of a needle guard in a protected position similar to FIG. 4A but wherein the insert is a plate with an opening and FIG. 4D is a sectional view of the needle guard of FIG. 4C.

FIG. 4A is a side view of a needle guard 400 located over a needle 202 in a protected position. The needle 202 has a substantially constant cross section, i.e., a nominal diameter, along the length of the needle 202 except for a change in profile 402 provided near the needle tip at the distal end of the needle 202. The change in profile may be viewed as a needle section having a different dimension than the nominal diameter and may be created using various means. In one embodiment, the change in profile 402 is made by crimping a portion of the needle 202, either along both sides or symmetrically along the circumference of the needle or alternatively only on one side or point on the circumference of the needle. The crimping process creates an indentation along one plane of the needle and an enlargement along another plane of the needle. The change in profile 402 may also be formed by adding material onto the outer surface of the needle 202 or by adding a sleeve to the needle. The added material may include an adhesive, a resin or a metal material. As such, the change in profile may be referred to as a bulge, which can include a section of the needle with added material, a crimp, a sleeve, a bulge, or combinations thereof.

Figure 4B:
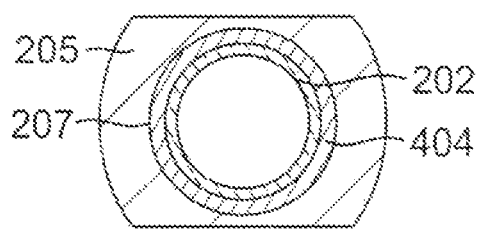

As shown in FIGS. 4A and 4B, the position of the change in profile 402 formed on the outer surface of the needle 202 is selected such that the change in profile 402 abuts or comes close to the distally facing side 62 of the base portion 205 of the needle guard 400 substantially at about the same time or moment as when the needle tip moves proximally of the angled end section 214 of the first arm 206. The change in profile 402, or at least the widest most point of the change in profile, is larger than the dimension of the bore 207 of the base portion 205. Thus, the needle tip of the needle 202 is prevented from moving proximally of the base portion 205 due to the relative dimensions of the change in profile 402 and the opening of the bore 207.

In some embodiments, the pull-off strength, detachment force, or separation force to separate the needle from the guard may be increased by incorporating an insert 404 to the bore 207. As shown in FIGS. 4A and 4B, instead of abutting directly against the material from which the needle guard 400 is made (e.g., plastic, elastomer, or TPE), the change in profile 402 may be made to at least partially abut the insert 404, which can be made from a metal, such as a stainless steel sleeve or tube. The metal-to-metal contact between the change in profile 402 and the metal insert 404 increases the pulling force required to pull the change in profile 402 through the bore 207 during use. In another embodiment instead of a metal insert, the insert may be made from a harder plastic material than the base material used to form the tip protector. By incorporating an insert 404 to the bore 207 of the tip protector 300, the detachment force can be made to increase by at least 100% over an opening made from a plastic, elastomer, or TPE material.

In one example, a detachment force to separate a needle from a polycarbonate tip protector has been found to be around 5 Newtons (N). Whereas with a metallic tip protector, separation is more difficult and a detachment force of about 20N or more, such as 30N, has been found to be achievable. Thus, a feature of the present device and method is a safety IVC comprising a needle hub, a catheter hub, and a tip protector made from a first material having an insert aligned with a proximal opening of the tip protector made from a second stronger material. Wherein a detachment force to separate the needle from the tip protector is at least 100% greater than a comparable safety IVC having a tip protector made only from the first material. For example, the detachment force can be 200%, 300%, or 400% greater than the comparable safety IVC having a tip protector made only from the first material. In a specific example, the detachment force is about 600% greater than a comparable safety IVC having a tip protector made only from the first material. Thus, an opening on the proximal wall or base section 205 of the tip protector may be enlarged easier by the change in profile located on the needle than for the opening of the insert element, which translates to greater detachment force.

Figure 4C:
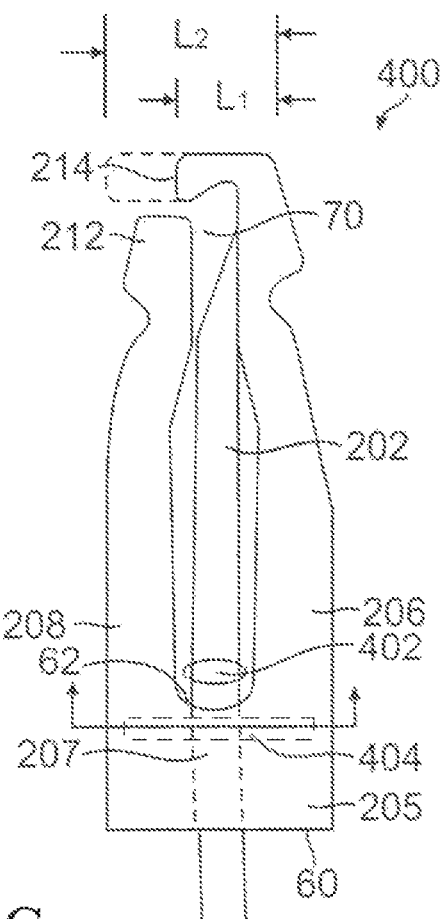
Figure 4D:
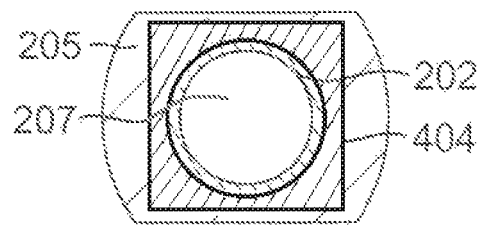

Thus, an aspect of the present safety IVC and method is a multi-piece tip protector made from a first material, such as an elastomer or TPE material, located at least partially within a catheter hub. Wherein an insert comprising an insert bore made from a second material is coupled to a proximal wall of the tip protector to form a multi-piece tip protector and to increase the detachment force of the multi-piece tip protector and a needle comprising a change in profile compared to similar safety IVCs where no insert is incorporated. In a particular embodiment, the insert is a metallic plate or sheet, as shown in FIGS. 4C and 4D. The coupling may be mechanical, co-molding or insert-molding, or bonding, such by adhesive or laser. In another embodiment, the insert is a metal sleeve or tube. In yet another embodiment, the insert increases the force required to pivot the needle, unintentionally or otherwise, relative to a bore of the proximal wall compared to the same safety IVCs without the insert. The insert comprises a bore or an opening that is aligned with the bore or opening of the needle guard. As previously described, the insert may be a plate or a sleeve and may be co-molded or insert molded with the needle guard or attached to an external surface of the needle guard.

A further aspect of the present device and method is a safety IVC comprising a tip protector made from a first material, such as an elastomer or a TPE, and having a proximal wall comprising an opening defining a bore and two arms extending distally of the proximal wall with one of the arms comprising an angled end section configured for covering a distal end of the other arm in a protective position; and wherein an insert made from a second material comprising an opening is aligned with the opening of the proximal wall. A further feature of safety IVC is a shield member made from a third material, which is different from the first material, coupled to the angled end section. In one example, the second material is the same as the third material. In still yet another example, the angled end section is both longer and wider than the distal end of the other arm.

Advantageously, use of the metal insert 404 to increase the pulling force allows for a reduction of the size of the change in profile 402. For example, when the change in profile is a crimp, the extent of crimping may be reduced when the change in profile is pulled against a base portion 205 of a non-metallic needle guard having an insert 404. This allows for the use of a more conventional catheter tube and fastening bush 203 (FIG. 2) used to affix the catheter tube to the catheter hub compared to a similar needle size used with a non-metallic needle guard without an insert. In other words, if an insert is not incorporated, a larger crimp may be required to prevent separation from the opening of the needle guard, which in turn requires a relative larger catheter tube to accommodate the larger crimp. Thus, by incorporating an insert, the needle crimp may be made to industry standard without having to over crimp the needle in an attempt to increase the detachment force, which requires a corresponding oversized catheter tube and fastening bush 203 to accommodate an otherwise enlarged crimp. Moreover, since the change in profile can be made smaller when used with a needle guard having an insert, the internal profile of the needle for enabling adequate fluid flow, which can decrease due to over crimping, can remain relatively large. Similarly, in embodiments in which the change in profile is made by adding material to the needle, the amount of material added to the needle to create the change in profile may also be reduced. Patients can benefit from the present design, which is configured to permit optimum crimping size and detachment force without having to oversize the needle and the catheter tube, which can lead to more painful venipuncture procedures. Said differently, the present device and method permit a relatively smaller needle size to be used compared to a similar safety IVC having a needle that is otherwise over crimped to work with a needle guard made from an elastomer or TPE without an insert.

Referring again to FIG. 4A, a tip holding space 70 is defined by an area behind the angled end section 214, the free end or cantilevered end 212 of the second arm 208, and the extent of travel when the needle 202 pivots side-to-side to move in and out from the plane defined by FIG. 4A. By sizing the angled end section with an appropriate length and width, the needle tip and the bevel section of the needle tip is retained within the tip holding space 70 regardless whether the needle pivots or rotates within the bore 207 and with or without an insert 404.

Figure 5:
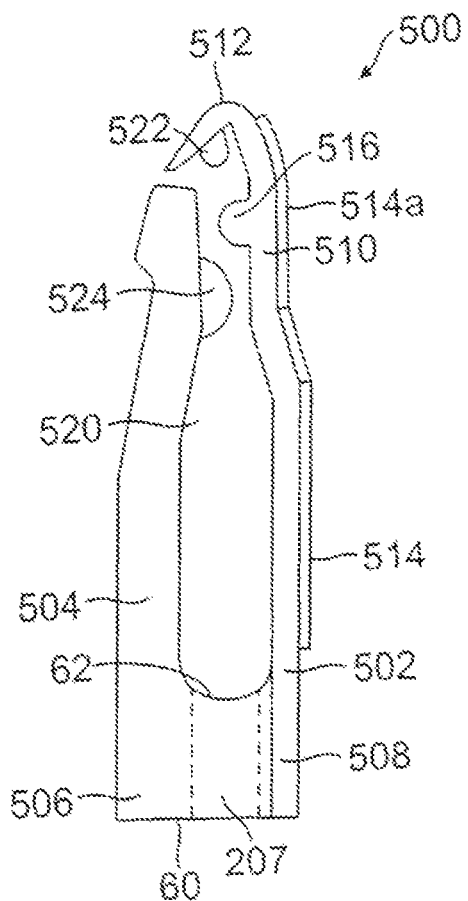
FIG. 5 is a side view of a needle guard in accordance with various embodiments.

FIG. 5 is a side view of a needle guard 500 provided in accordance with another embodiment of the present assembly and method. As shown, the first arm 502 and the second arm 504 may each be made either completely or partially of a metal material. For example, the first arm 502 of the needle guard 500 may be made from a metal material but not the second arm, which may be made from a plastic, an elsastomer, or a TPE. The metallic first arm 502 may be coupled to the second arm 504 of the needle guard 500 using known prior art means, such as by insert-molding, welding or by adhesive. In some embodiments, the metal first arm 502 is attached to a base portion 506 of the needle guard 500. In the embodiment shown, the base portion 506 is made from the same material as the second arm 504. In other embodiments, the base portion 506 is made from a metal material. The base portion 506 of the various embodiments includes a bore 207 extending therethrough in the axial direction for receiving the needle 202. The base portion 506 further has proximally 60 and distally 62 facing wall surfaces.

In one embodiment, the first arm 502 may be formed from a strip of sheet metal having spring-like properties. In this embodiment, the first arm 502 includes a base section 508 and a deflectable section 510. The base section 508 is coupled to the base portion 506. In one embodiment, the base section 508 of the first arm 502 lies against an outer surface of the base portion 506. The base section 508 of the first arm 502 may be secured to the base portion 506 using conventional methods, such as by adhesive, welding or insert-molding.

Figure 6:
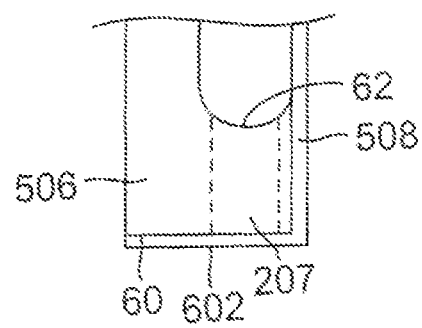
FIG. 6 is a sectional view of an alternative configuration of the needle guard of FIG. 5 in accordance with an embodiment.

In an alternative embodiment shown in FIG. 6, a proximal face 602 may be created by bending a portion of the base section 508 of the first arm 502 around the base portion 506 of the needle guard to lie against the proximal outer surface 60 of the base portion 506. In this embodiment, the bottom face 602 defines a hole that lies concentrically with the bore 207 to allow the needle 202 to be inserted therethrough. The bottom face 602 is configured to increase the pulling force required to pull the change in profile 402 completely through the bore 207 during use, i.e., the detachment force. In another embodiment, the bottom face 602 is insert-molded to the needle guard and is positioned internally of the base portion 506 or on the distal wall surface of the base portion. Optionally, the base portion 506 also includes an insert 404 in addition to the bottom face 602.

Referring again to FIG. 5, the deflectable section 510 of the first arm 502 includes a distal angled end section 512. The angled end section 512 is angled inwards, towards the second arm 504. The angled end section 512 may have a length that extends over at least a fraction of a percent to over 100% of the second arm 504. In one embodiment, the angled end section 512 may have a generally V-shape with the peak of the V pointing in the axial direction and the free leg of the V extending in the direction of the second arm 504.

In one embodiment, one or more rib members 514 may be added to the first arm 502. The rib members 514 are provided on the first arm 502 to add strength to the arm. To provide the added strength, the rib members 514 may extend axially along the entire length of the first arm 502 or may extend only along a portion of the first arm 502. For example, a rib member may extend substantially along only the axial length of the deflectable section 510. When the deflectable section 510 of the first arm 502 is biased away from the second arm 504, the rib member 514a increases the amount of resistance with which the first arm resists the biasing. Thus, when the biasing is removed, the deflectable section 510 of the first arm 502 is more quickly and reliably moved back to the protected positioned. In addition, once in the protected position, the stiffening of the first arm 502 by the rib member 514a makes it more difficult to inadvertently deflect the deflectable section 510 of first arm 502.

In one embodiment, the needle guard 500 may include one or a pair of flaps 516. The flaps 516 may be included as an extension of the first arm 502 that are bent 90 degrees or more towards the open area 520. The flaps 516 extend from the first arm 502 into an open area 520 defined in the open space between the first arm 502 and the second arm 504. In this manner, the flaps 516 provide a semi-closure to the open area 520, which helps to keep the needle tip confined behind the angled end section 512.

Alternatively, or in addition to, the flaps 522 may be positioned on the angled end section 512. The flaps 522 may be made as extensions of a top and bottom surface of the angled end section 512. The flaps 516 and 522 may be formed integrally with the corresponding first arm 502 and angled end section 512. The flaps may also later be attached to the corresponding first arm 502 and angled end section 512, such as by using an adhesive, by welding the flaps thereto or by using other similarly suitable attaching methods known in the art.

In embodiments in which the second arm 504 is made of a non-metal, metal or non-metal flaps 524 may be added to the second arm. The flaps 524 may be added using adhesives or other similarly suitable attaching methods known in the art. The second arm may be made completely or partially out of metal.

In each embodiment, the flaps 516, 522 and 524 are dimensioned such that the needle tip is blocked from exiting the open area 520 when the first and second arms 502 and 504 are in the protected position. For example, the flaps 516 and 524 may extend from each arm into the open area 520 a distance up to or over the axial centerline of the needle guard 500. In another example, the flaps 522 may extend from the angled end section 512 into the open area 520 a distance that causes the flaps 522 to protrude over a portion of the needle 202.

The above description presents the best mode contemplated for establishing a needle safety device and associated methods and of the manner and process of making and using it in such full, clear, concise, and exact terms as to enable any person skilled in the art to which it pertains to make and use this apparatus. This apparatus is, however, susceptible to modifications and alternate constructions from that discussed above that are fully equivalent. Consequently, this apparatus is not limited to the particular embodiments disclosed and certain features disclosed for one embodiment may be incorporated in another embodiment provided their functions are compatible. On the contrary, this apparatus covers all modifications and alternate constructions coming within the spirit and scope of the apparatus as generally expressed by the following claims, which particularly point out and distinctly claim the subject matter of the apparatus. Further, the embodiments illustratively disclosed herein suitably may be practiced in the absence of any element, which is not specifically disclosed herein.

What is claimed is:

1. A needle assembly comprising:
   a needle guard having a non-metallic base portion comprising a wall having a bore, a bore length, a bore diameter, a proximally facing surface, and a distally facing surface;
   a first arm including a first free end and a second arm including a second free end, the first and second arms extending generally axially in a distal direction from the non-metallic base portion, the first free end extending beyond the second free end and including an angled end section that extends toward the second arm, the angled end section comprising a first side edge, a second side edge, a length, and a width;
   an open area, an open space, or a needle tip holding space defined at least in part by the non-metallic base portion, the first arm, the second arm, and the angled end section;
   an insert located at the non-metallic base portion, said insert being made from a different material than a material of the non-metallic base portion and said insert having an opening aligned with the bore of the non-metallic base portion;
   a needle having a tip and an outer diameter, the needle passing through the bore of the non-metallic base portion and the opening of the insert;
   wherein the first arm and the second arm are biased so as to move between a ready position in which the angled end section abuts a side of the needle and a protected position in which the needle tip is confined within the open area, the open space, or the needle tip holding space; and
   wherein the width of the angled end section is at least 2.5 times larger than the outer diameter of the needle, and wherein a combination of the length and width of the angled end section, the bore length and the bore diameter is configured to retain the needle tip within the open area, the open space, or the needle tip holding space in the protected position, even when the needle rotates or both pivots and rotates.

2. The needle assembly of claim 1, wherein the length and width of the angled end section and the bore length and the bore diameter of the non-metallic base portion cooperate to prevent the needle tip from moving beyond the first side edge or the second side edge.

3. The needle assembly of claim 1, wherein the insert is cylindrical and is made from a metallic material.

4. The needle assembly of claim 3, wherein the insert has a length with a bore and wherein the bore of the insert is coaxial with the bore of the non-metallic base portion.

5. The needle assembly of claim 3, wherein the insert is attached to the non-metallic base portion.

6. The needle assembly of claim 1, further comprising a tensioning member for biasing the first arm and the second arm toward one another.

7. The needle assembly of claim 1, further comprising a shield member made from a different material than the non-metallic base portion located at the angled end section.

8. The safety catheter assembly of claim 1, wherein the length of the angled end section protrudes over at least a portion of the second free end in the protected position.

9. The safety catheter assembly of claim 1, wherein the angled end section protrudes over a fraction of the second free end, between 40% to 100% of the second free end, or over 100% of the second free end when in the protected position.

10. The safety catheter assembly of claim 1, further comprising a crimp on the needle for engaging the insert.

11. The safety catheter assembly of claim 1, wherein the width of the angled end section is at least 1.5 times larger than the width of the second free end.

12. A needle assembly comprising:
   a needle guard having a non-metallic base portion comprising a wall having a bore, a bore length, a bore diameter, a proximally facing surface, and a distally facing surface;
   a first arm including a first free end and a second arm including a second free end, the first and second arms extending generally axially in a distal direction from the non-metallic base portion, the first free end extending beyond the second free end and including an angled end section that extends toward the second arm, the angled end section comprising a first side edge, a second side edge, a length, and a width;

an open area, an open space, or a needle tip holding space defined at least in part by the non-metallic base portion, the first arm, the second arm, and the angled end section;

an insert located at the non-metallic base portion, said insert being made from a different material than a material of the non-metallic base portion and said insert having an opening aligned with the bore of the non-metallic base portion;

a needle having a tip and an outer diameter, the needle passing through the bore of the non-metallic base portion and the opening of the insert;

wherein the first arm and the second arm are biased so as to move between a ready position in which the angled end section abuts a side of the needle and a protected position in which the needle tip is confined within the open area, the open space, or the needle tip holding space;

wherein the width of the angled end section is at least 2.5 times larger than the outer diameter of the needle, and wherein a combination of the length and width of the angled end section, the bore length and the bore diameter is configured to retain the needle tip within the open area, the open space, or the needle tip holding space in the protected position, even when the needle rotates or both pivots and rotates; and wherein the needle comprises a change in profile and wherein the change in profile is configured to abut a perimeter defining the opening of the insert.

13. The safety catheter assembly of claim 12, wherein the width of the angled end section is at least 1.5 times larger than the width of the second free end.

14. The safety catheter assembly of claim 12, further comprising a shield member made from a different material than the non-metallic base portion located at the angled end section.

15. The safety catheter assembly of claim 12, wherein the angled end section protrudes over a fraction of the second free end, between 40% to 100% of the second free end, or over 100% of the second free end when in the protected position.

16. A needle assembly comprising:
a needle guard having a non-metallic base portion comprising a wall having a bore, a bore length, a bore diameter, a proximally facing surface, and a distally facing surface;
a first arm including a first free end and a second arm including a second free end, the first and second arms extending generally axially in a distal direction from the non-metallic base portion, the first free end extending beyond the second free end and including an angled end section that extends toward the second arm, the angled end section comprising a first side edge, a second side edge, a length, and a width;

an open area, an open space, or a needle tip holding space defined at least in part by the non-metallic base portion, the first arm, the second arm, and the angled end section;

an insert located at the non-metallic base portion, said insert being made from a different material than a material of the non-metallic base portion;

a needle having a bevel, a tip at an end of the bevel, and an outer diameter passing through the bore of the non-metallic base portion;

wherein the first arm and the second arm are biased so as to move between a ready position in which the angled end section abuts the needle and a protected position in which the needle tip is confined within the open area, the open space, or the needle tip holding space; and wherein the width of the angled end section is at least 2.5 times greater than the outer diameter of the needle to prevent the bevel from contacting the first side edge or the second side edge of the angled end section, and wherein a combination of the length and width of the angled end section, the bore length and the bore diameter is configured to retain the needle tip within the open area, the open space, or the needle tip holding space in the protected position, even when the needle rotates or both pivots and rotates.

17. The safety catheter assembly of claim 16, wherein the length of the angled end section protrudes over at least a portion of the second free end in the protected position.

18. The safety catheter assembly of claim 16, wherein the angled end section overlaps the second free end of the second arm in the protected position, from between 40% to 100% of the second free end.

19. The safety catheter assembly of claim 16, wherein the angled end section protrudes over a fraction of the second free end, between 40% to 100% of the second free end, or over 100% of the second free end when in the protected position.

20. The needle assembly of claim 16, wherein the width of the angled end section is 300% greater than the outer diameter of the needle.

21. The needle assembly of claim 16, wherein the angled end section overlaps the second free end of the second arm in the protected position.

22. The needle assembly of claim 21, wherein the needle passes through the bore and an opening on the insert in the ready position.

* * * * *